United States Patent
Riegelsberger et al.

(10) Patent No.: US 11,850,007 B2
(45) Date of Patent: Dec. 26, 2023

(54) TRACKER FOR A SURGICAL NAVIGATION SYSTEM

(71) Applicant: Stryker European Operations Holdings LLC, Kalamazoo, MI (US)

(72) Inventors: Fabian Riegelsberger, Umkirch (DE); Florian Herrmann, Schwanau (DE); Jochen Breisacher, Teningen (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 174 days.

(21) Appl. No.: 16/745,470

(22) Filed: Jan. 17, 2020

(65) Prior Publication Data
US 2020/0229873 A1  Jul. 23, 2020

(30) Foreign Application Priority Data

Jan. 22, 2019 (EP) .................................. 19153075

(51) Int. Cl.
  *A61B 34/20* (2016.01)
  *A61B 17/70* (2006.01)
  *A61B 17/34* (2006.01)

(52) U.S. Cl.
  CPC .......... *A61B 34/20* (2016.02); *A61B 17/3403* (2013.01); *A61B 17/7002* (2013.01); *A61B 2034/2055* (2016.02); *A61B 2034/2057* (2016.02)

(58) Field of Classification Search
  USPC ....................................................... 600/424
  See application file for complete search history.

(56) References Cited

U.S. PATENT DOCUMENTS

| | | | |
|---|---|---|---|
| 6,336,904 B1 * | 1/2002 | Nikolchev | A61B 5/0084 600/562 |
| RE39,102 E | 5/2006 | Schulz et al. | |
| 7,444,178 B2 | 10/2008 | Goldbach | |
| 2002/0038121 A1 * | 3/2002 | Rozenberg | A61B 90/39 606/15 |
| 2004/0002642 A1 | 1/2004 | Dekel et al. | |

(Continued)

FOREIGN PATENT DOCUMENTS

| | | |
|---|---|---|
| EP | 1920730 A2 | 5/2008 |
| WO | 2009049038 A1 | 4/2009 |
| WO | 2015022100 A1 | 2/2015 |

OTHER PUBLICATIONS

English language abstract for EP 1 920 730 A2 extracted from espacenet.com database on Apr. 6, 2023, 1 page.

*Primary Examiner* — Jason M Ip
*Assistant Examiner* — Renee C Langhals
(74) *Attorney, Agent, or Firm* — Howard & Howard Attorneys PLLC

(57) ABSTRACT

A tracker, a surgical tool system, a surgical navigation system, and a method for operating a surgical navigation system are provided. The tracker is configured to be associated with a patient or a surgical tool that is to be tracked by the surgical navigation system. The tracker comprises an optical fibre having a longitudinal extension and configured to be optically coupled to a light source such that the optical fibre transmits light emitted by the light source. The optical fibre has a lateral surface along its longitudinal extension and is configured to emit light via at least a portion of the lateral surface.

19 Claims, 14 Drawing Sheets

(56) References Cited

U.S. PATENT DOCUMENTS

| | | | |
|---|---|---|---|
| 2006/0142657 A1* | 6/2006 | Quaid | A61B 90/37 |
| | | | 600/424 |
| 2006/0285350 A1* | 12/2006 | Wang | G02B 6/001 |
| | | | 362/555 |
| 2008/0194973 A1 | 8/2008 | Imam | |
| 2011/0060216 A1* | 3/2011 | Foley | A61B 17/8872 |
| | | | 600/426 |
| 2011/0270080 A1 | 11/2011 | Crane | |
| 2015/0327948 A1* | 11/2015 | Schoepp | A61B 34/20 |
| | | | 600/424 |
| 2019/0053851 A1* | 2/2019 | Siemionow | A61B 34/20 |
| 2019/0142522 A1* | 5/2019 | Jajal | A61B 34/25 |
| | | | 600/424 |
| 2021/0063722 A1* | 3/2021 | Dhaliwal | A61B 1/00165 |

\* cited by examiner

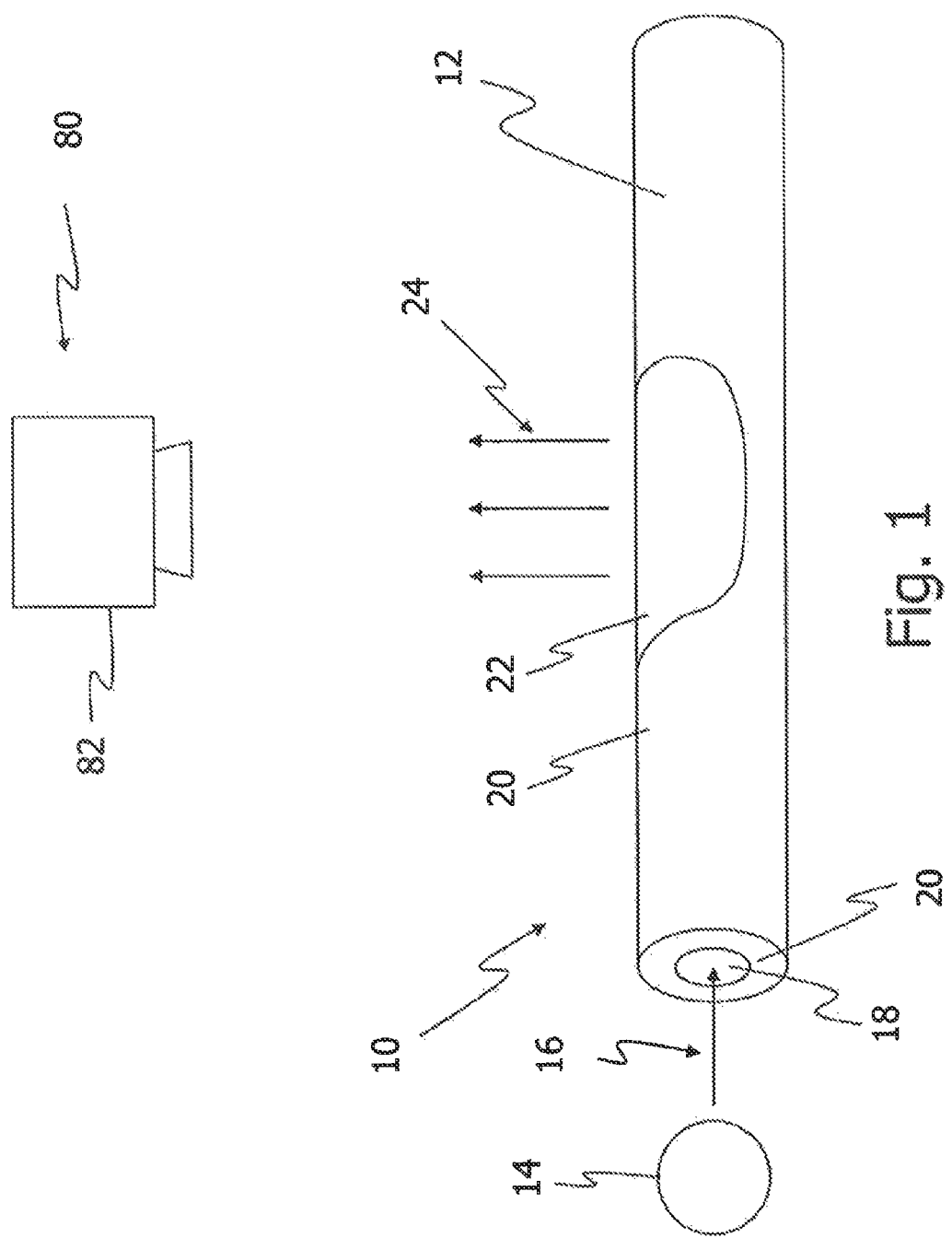

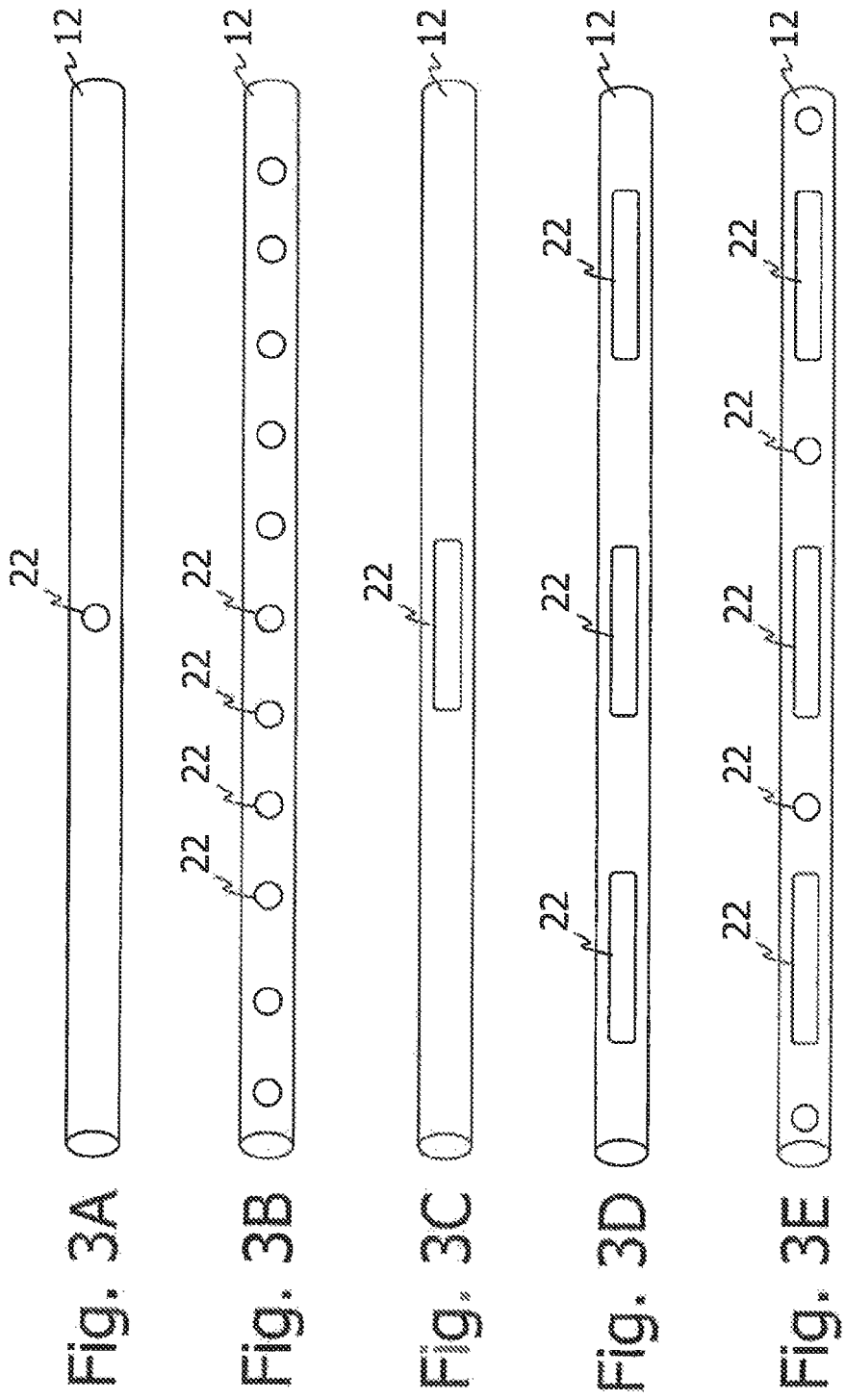

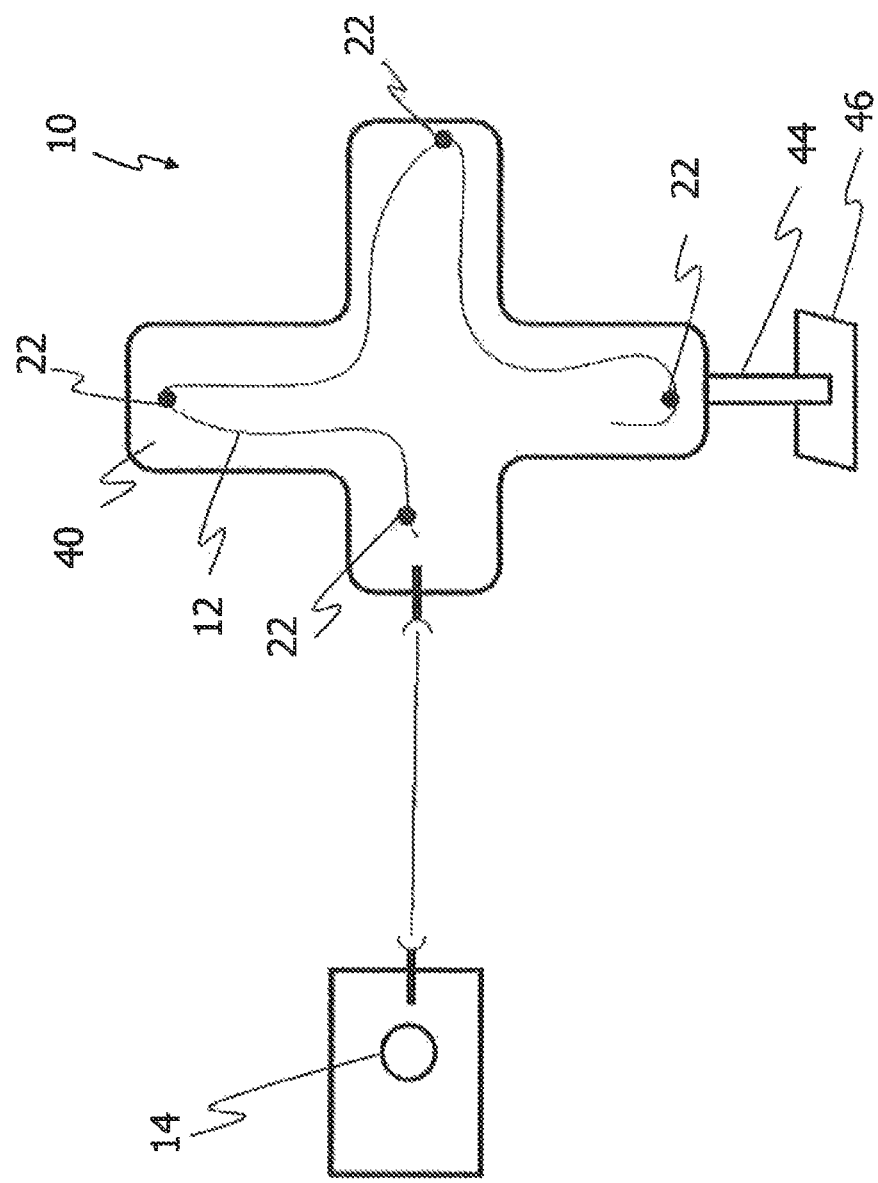

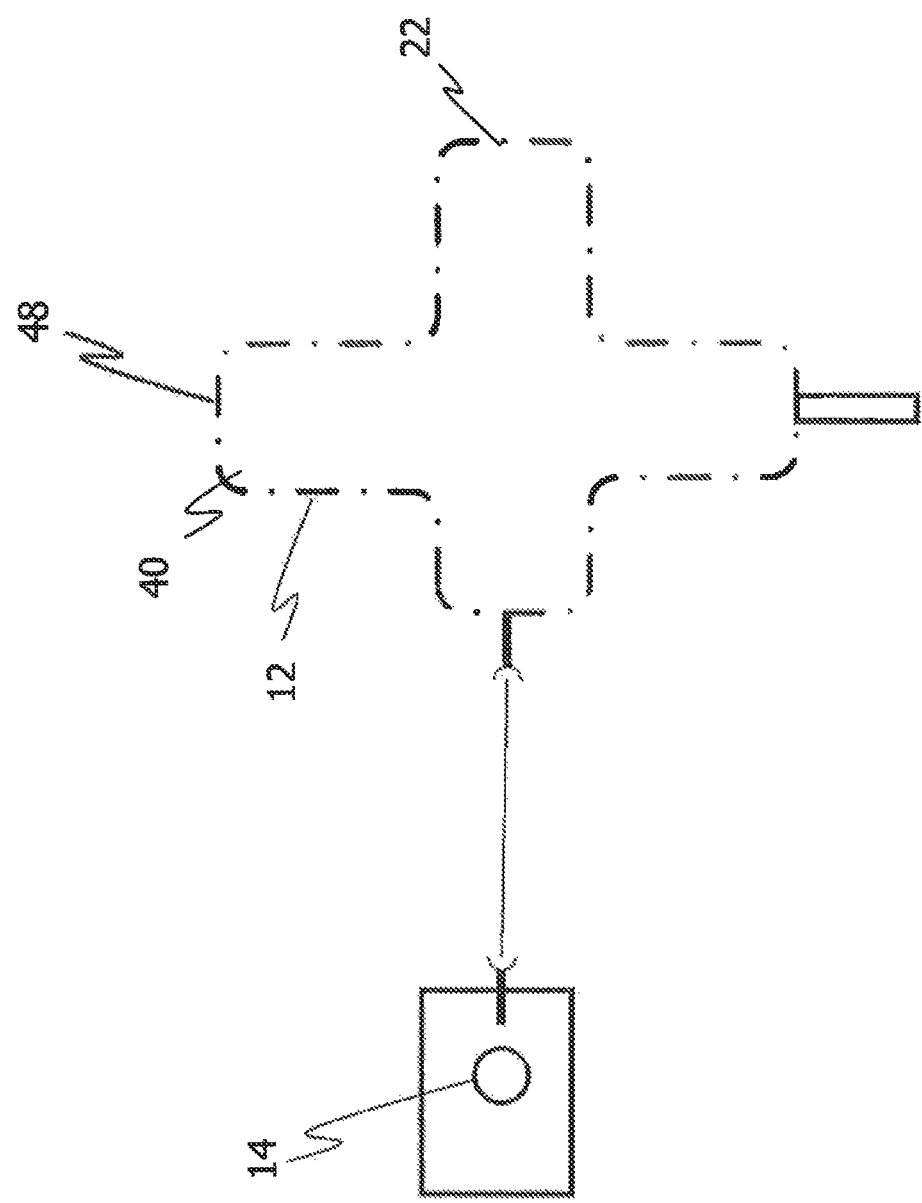

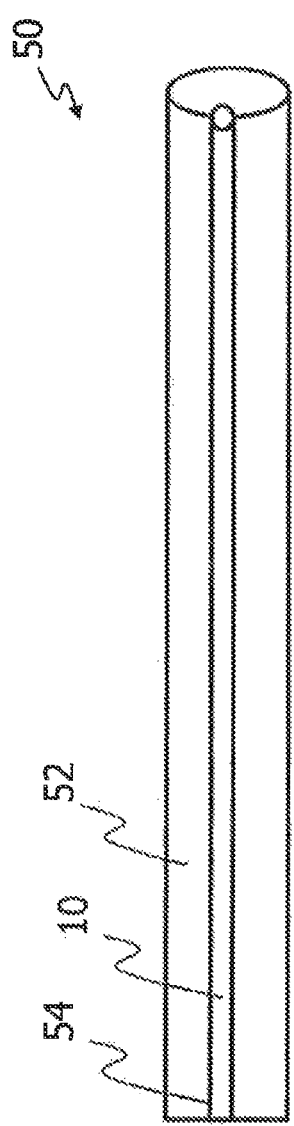
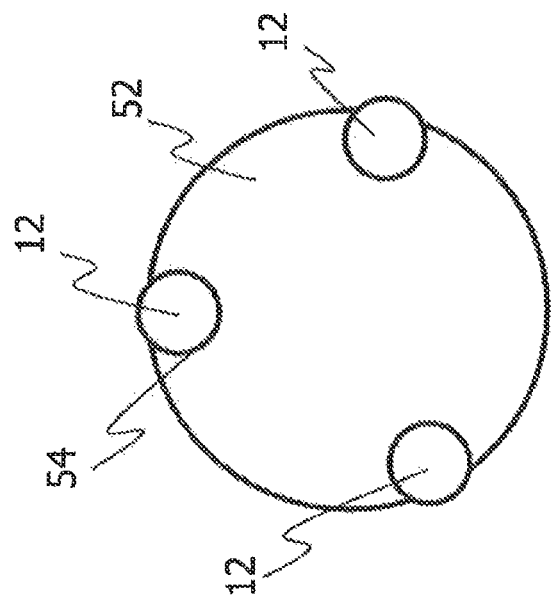
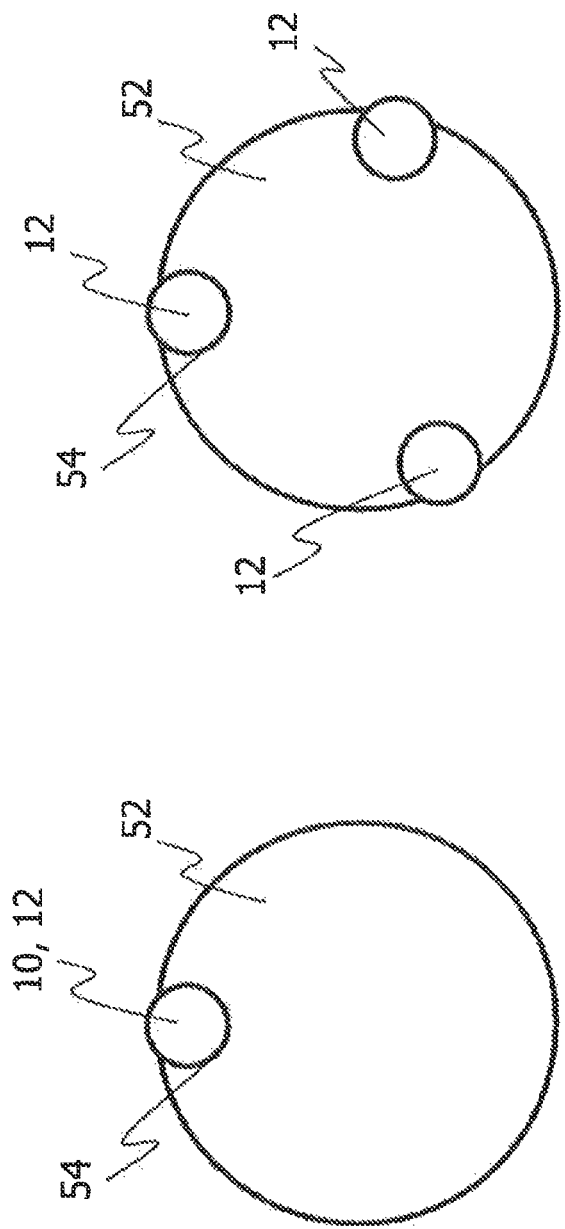

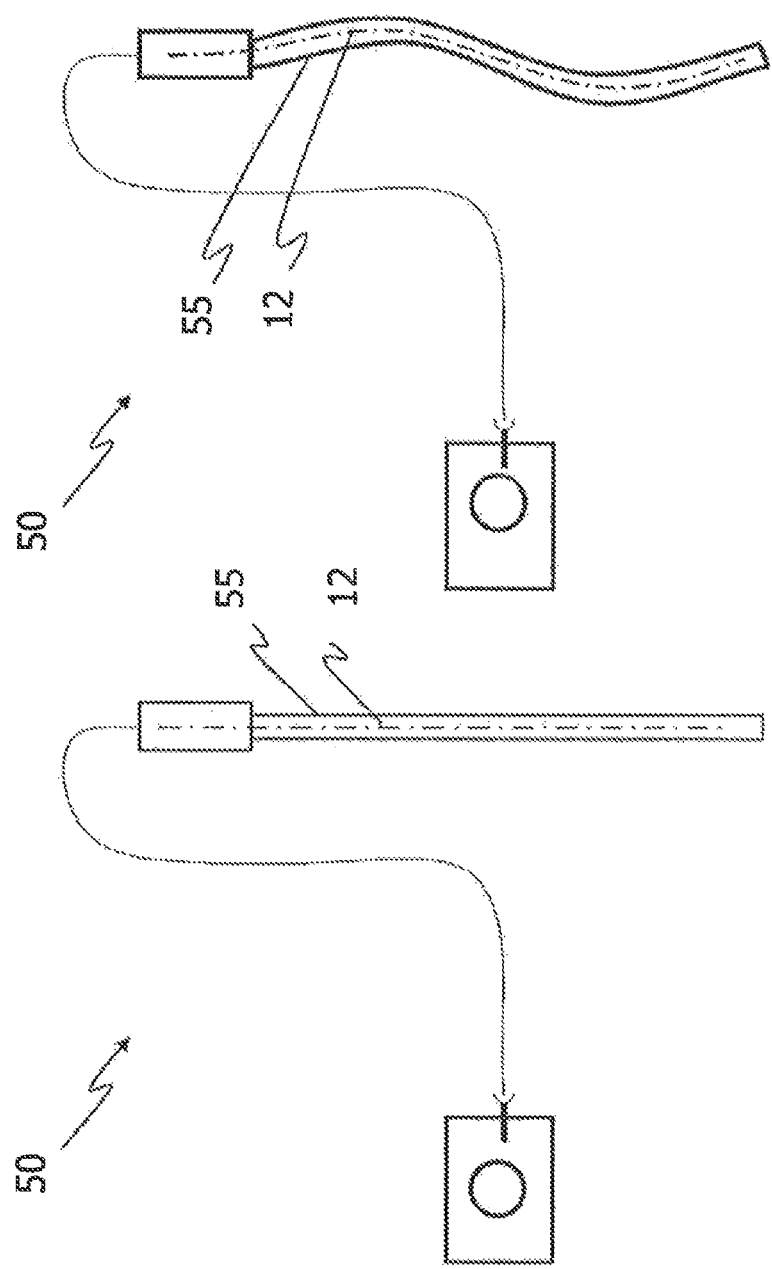

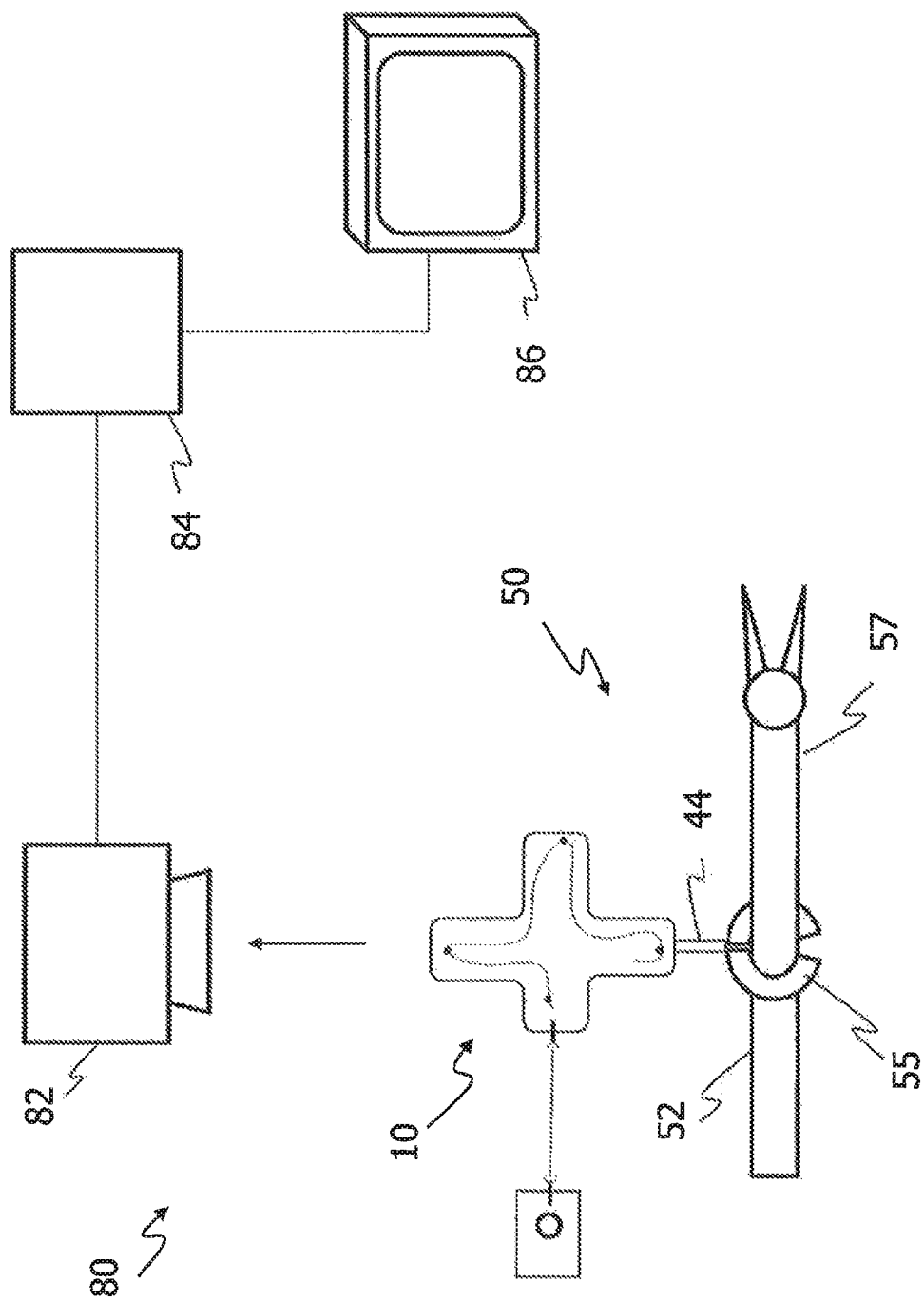

TRACKER FOR A SURGICAL NAVIGATION SYSTEM

PRIORITY CLAIM

This application claims priority under 35 U.S.C. § 119 to European Patent Application No. 19153075.7, filed Jan. 22, 2019, the entire contents of which are hereby incorporated by reference.

TECHNICAL FIELD

The present disclosure generally relates to a tracker for use in surgical navigation. In particular, a tracker comprising an optical fibre and configured to be tracked by a surgical navigation system is presented.

BACKGROUND

Many surgical procedures benefit from determining a position and orientation (i.e., a pose) of surgical objects such as surgical tools and a patient. A surgical navigation system allows tracking of a surgical object and calculating a pose of the surgical object relative to registered three dimensional image data of the patient.

In a typical application of a surgical navigation system, a surgical tool and the patient are each associated with a tracker, wherein three dimensional image data previously obtained by, for example, a CT scan is registered with the patient tracker. By tracking the patient and the surgical tool, the surgical navigation system can determine the pose of both surgical objects and calculate a spatial relationship between the surgical tool and the three dimensional image data. The determined spatial relationship can, for example, be displayed on a screen, helping the surgeon guide the surgical tool relative to the patient.

A common type of a surgical navigation system is an optical navigation system which comprises an optical sensor that senses light emitted by the tracker. As light sources, light emitting diodes are often used due to their high efficiency and ability to generate small light spots. In order to determine the pose of the tracker, a plurality of light sources need to be detected by the optical sensor, wherein a higher degree of freedom requires a larger number of light sources. However, a large number of light sources results in a higher weight of the tracker and more complex circuitry.

SUMMARY

There is a need for a tracker that solves one or more of the aforementioned or other problems.

According to one aspect, a tracker configured to be associated with a patient or a surgical tool that is to be tracked by a surgical navigation system is provided. The tracker comprises an optical fibre having a longitudinal extension and configured to be optically coupled to a light source such that the optical fibre transmits light emitted by the light source. The optical fibre has a lateral surface along its longitudinal extension and is configured to emit light via at least a portion of the lateral surface.

The optical fibre may comprise a plurality of light emitting portions that are spaced apart along its longitudinal extension. The spacing between the light emitting portions may have a non-periodic or a periodic pattern. The plurality of light emitting portions may be spaced equally apart along the longitudinal extension of the optical fibre.

The at least one light emitting portion may extend longitudinally along the optical fibre. The light emitting portion may extend along the entire optical fibre. The optical fibre may have a plurality of light emitting portions that extend longitudinally along the optical fibre. In such a case, the light emitting portions may have the same length. Alternatively, the light emitting portions may have different lengths.

The at least one light emitting portion may be confined to an essentially point-shaped spot on the optical fibre. The longitudinal extension of the point-shaped light emitting portion may be shorter than 2 times, preferably 1 time, or more preferably 0.5 times the diameter of the optical fibre. In case the optical fibre has a plurality of light emitting portions, each light emitting portion may be an essentially point-shaped spot. Alternatively, the optical fibre may comprise at least one light emitting portion that extends longitudinally along the optical fibre and at least one light emitting portion that is confined to an essentially point-shaped spot on the optical fibre.

The optical fibre may comprise a core and a cladding around the core, wherein the at least one light emitting portion is defined by an area of the optical fibre at which the cladding has at least one of an opening, a higher refractive index than the surrounding cladding and a smaller wall thickness than the surrounding cladding. The corresponding area of the optical fibre may be the result of at least one of laser irradiation, mechanical ablation, kinking of the optical fibre, chemical treatment, and using different materials for the manufacturing of the cladding and/or of the core. The corresponding area may extend around the entire circumference or a part of the circumference of the optical fibre.

The tracker may further comprise a light absorbing sleeve configured to encase at least a part of the optical fibre, wherein the sleeve defines an area with an opening or a reduced light absorbance. The sleeve may extend over the entire or part of the length of the optical fibre. A part or the entire optical fibre may be configured to emit light via a lateral surface of the optical fibre, wherein the emitted light is absorbed by the sleeve in areas where the encasing sleeve has no opening or reduced light absorbance. The area of the opening or the reduced light absorbance may extend around the entire circumference or a part of the circumference of the optical fibre. The longitudinal extension of the region of the opening or the reduced light absorbance may be shorter than 2 times, preferably 1 time, or more preferably 0.5 times the diameter of the optical fibre.

The optical fibre may have two opposite ends, wherein both ends of the optical fibre are configured to be optically coupled to the light source. Both ends of the optical fibre may be coupled to the light source. The tracker may comprise a plurality of optical fibres. Each fibre can be coupled to a respective light source. Alternatively, a plurality of optical fibres may be coupled to a common light source. One end of each of the plurality of the optical fibres may be coupled to one light source and the other end of each of the plurality of light sources may be coupled to the one light source or another light source.

The tracker may comprise the light source. The light source may comprise a light emitting diode, a laser, an organic light emitting diode, a polymer light emitting diode, a fluorescent lamp or an incandescence light source. The light source may operate in at least one of the infrared light spectrum, visible light spectrum, and ultraviolet light spectrum.

The optical fibre may be configured to be stretchable in a direction along its longitudinal extension. When attached to the surface of patient, the optical fibre may be stretchable in such a way that the optical fibre adapts to movement of the surface of the patient.

The tracker may comprise a carrier, wherein the optical fibre is supported by the carrier. At least a part of the optical fibre may be arranged at least one of on, in and below a surface of the carrier. In case the tracker comprises the light source, the light source may be supported by the carrier.

The carrier may have an edge, wherein the optical fibre extends along the edge. The edge may be arranged in a plane. An edge may be defined by a line segment where two surfaces of the carrier meet at an angle different than zero.

The carrier may comprise a translucent material, wherein at least a part of the optical fibre is embedded inside the carrier. The translucent material may be translucent for a selected spectral range. The selected spectral range may comprise at least one of infrared light, visible light, and ultraviolet light. The carrier may comprise transparent material.

The carrier may be flexible. The carrier may be compressible. The carrier may have a flexibility that allows the carrier to adapt to the shape of the surface of the patient.

The carrier may have the shape of a frame enclosing a central opening. The shape of the frame may be rectangular, oval, circular or polygonal. The central opening may be configured to frame a surgical site. The optical fibre may extend along at least a part of the frame. Alternatively, the carrier may have the shape of an elongated strip. The elongated strip may extend in a straight line or may have a meandering shape. The optical fibre may extend along at least a part of the elongated strip or the meandering shape.

The tracker may further comprise an interface configured to couple the tracker to the patient or the surgical tool. The interface may comprise an adhesive and/or a clamp. Additionally or alternatively, the interface may comprise at least one of a screw, a snap-in-connector, and a magnet.

According to a second aspect, a surgical tool system is provided. The surgical tool system comprises a tracker as described herein and the surgical tool coupled to the tracker.

The surgical tool may comprise a recess configured to receive at least a part of the optical fibre. The at least part of the optical fibre may be fixed in the recess by at least one of a glue, form-fit manner, a strut, and a translucent lid. The surgical tool may comprise a plurality of recesses that are configured to each receive one of a plurality of optical fibres.

The surgical instrument may comprise a surgical rod, wherein at least a part of the optical fibre of the tracker extends along at least a portion of the surgical rod. The optical fibre may extend essentially in the same direction as the surgical rod.

The surgical rod may be configured to be attachable to at least one vertebra. The surgical rod may be configured to be attachable to a screw that is screwed or screwable into a vertebra. The surgical rod may be bendable.

The surgical tool may comprise a surgical needle, wherein at least a part of the optical fibre extends along a portion of the surgical needle. The optical fibre may extend essentially in the same direction as the surgical needle. The surgical needle may be bendable. The surgical needle may comprise a hollow tube separate from the optical fibre for injecting fluids into and/or extracting fluids from a patient.

According to a third aspect, a surgical navigation system is provided. The surgical navigation system comprises at least one of the tracker and the surgical tool system as described herein and an optical sensor configured to detect light emitted by the optical fibre. The optical sensor may comprise at least one camera. The optical sensor may comprise a mono camera and/or a stereo camera. The optical sensor may be configured to have an increased sensitivity for an optical spectrum emitted by the light source. The higher sensitivity may be realized by an optical filter or circuitry that filters sensor signal data dependent on its associated wavelength. The surgical navigation system may further comprise a navigation controller configured to receive sensor data by the optical sensor. The navigation controller may further be configured to calculate a position and/or an orientation of the tracker in a coordinate system of the surgical navigation system based on the detected light.

According to a fourth aspect, a method of operating a surgical navigation system that comprises an optical sensor and a tracker is provided. The tracker comprises an optical fibre having a longitudinal extension and is configured to be optically coupled to a light source such that the optical fibre transmits light emitted by the light source, wherein the optical fibre has a lateral surface along its longitudinal extension and is configured to emit light via at least a portion of the lateral surface. The method comprises the step of detecting, by the optical sensor, light emitted by the portion of the lateral surface of the optical fibre. The method further comprises the step of calculating at least one of a position and an orientation of the tracker in a coordinate system of the surgical navigation system based on the detected light.

The tracker may be part of a surgical tool system comprising the tracker and a surgical rod, wherein at least a part of the optical fibre of the tracker extends along at least a portion of the surgical rod. In such a case, the method may further comprise the step of determining a current longitudinal extension of the surgical rod in the coordinate system of the surgical navigation system. The method may further comprise determining at least one of a target shape, target position and target orientation of the surgical rod. The method may further comprise outputting instructions for at least one of reshaping, repositioning and reorienting of the surgical rod into the determined at least one of target shape, target position and target orientation.

A shape matching algorithm may be used in the context of the reshaping procedure. For this purpose, the light emitting portion may stretch along a substantial length of the optical fibre.

The outputting of the instructions may comprise displaying at least one of target shape, target position and target orientation in a visual representation of three dimensional image data of the patient.

BRIEF DESCRIPTION OF THE DRAWINGS

Further details, advantages and aspects of the present disclosure will become apparent from the following embodiments taken in conjunction with the drawings, wherein:

FIG. 1 shows a first embodiment of a tracker;

FIG. 3A-E shows an optical fibre with different configurations for the light emitting portions;

FIG. 7 shows a fifth embodiment of a tracker comprising a carrier;

FIG. 8 shows a sixth embodiment of a tracker, wherein the optical fibre extends along an edge of the carrier;

FIG. 9A shows a first embodiment of a surgical tool system;

FIG. 9B shows a cross-section of the surgical tool system of FIG. 9A;

FIG. 9C shows a cross-section of a second embodiment of a surgical tool system;

FIG. 12A shows a forth embodiment of the surgical tool system with a tracker attached to a surgical needle;

FIG. 12B shows the fourth embodiment of the surgical tool system of FIG. 12A, wherein the surgical needle is bent;

FIG. 13 shows a surgical navigation system comprising a tracker and an optical sensor.

DETAILED DESCRIPTION

Figure 2A:
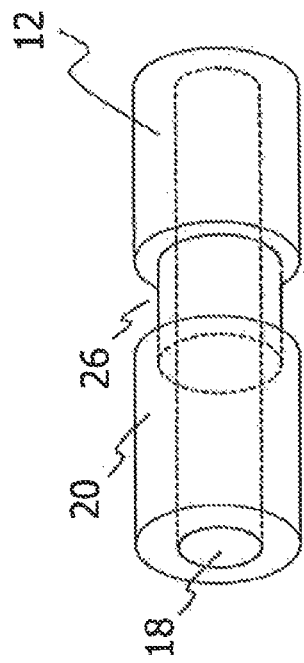
FIG. 2A shows an optical fibre with a circumferential light emitting portion.

In the following description, exemplary embodiments of a tracker for surgical navigation, a surgical tool system, a surgical navigation system and a method for operating a tracker will be explained with reference to the drawings. The same reference numerals will be used to denote the same or similar structural features.

FIG. 1 shows a first embodiment of a tracker 10 to be associated with a patient or a surgical tool that is to be tracked by a surgical navigation system 80. The tracker 10 comprises an optical fibre 12 having a longitudinal extension that is configured to be optically coupled to a light source 14. The light source 14 emits light 16. In the drawings, light is illustrated with straight arrows. The optical fibre 12 is coupled to the light source 14 such that the optical fibre 12 transmits light 16 emitted by the light source 14.

To this end, the optical fibre 12 comprises a core 18 and a cladding 20 surrounding the core 18. The core 18 is essentially wire shaped and comprises a material that is transparent at least for a part of the spectrum of the light 16 emitted by the light source 14. The cladding 20 is essentially tube shaped and also comprises a material that is transparent at least for a part of the spectrum of the light 16 emitted by the light source 14. However, the material of the core 18 and the material of the cladding 20 have a different refractive index, which results in a boundary that is configured to reflect light from the core 18 that impinges the boundary back into the core 18.

In the present embodiment of the tracker 10, the refractive index of the core material is higher than that of the cladding material. In such a configuration, light impinging the boundary under an angle larger than the critical angle $\theta_c$ for the boundary is completely reflected. The critical angle for the boundary can be calculated using the following equation:

$$\theta_c = \arcsin\left(\frac{n_2}{n_1}\right)$$

with the critical angle $\theta_c$, the refractive index of the core material $n_1$ and the refractive index of the cladding material $n_2$.

The light 16 from the light source 14 is coupled into the optical fibre 12 in such a way that most of the light impinges the boundary at a steep angle below the critical angle $\theta_c$ and is therefore reflected totally at the boundary. Unless the optical fibre 12 is bent at large angles, light inside the core 18 keeps being totally reflected and therefore essentially without losses. Therefore, the optical fibre 12 acts like a wave guide.

The optical fibre 12 has a lateral surface 20 along its longitudinal extension. The lateral surface 20 has a portion 22 at which the optical fibre 12 is configured to emit light 24. The surgical navigation system 80 comprises a light sensor 82 that is configured to detect the light 24 emitted by the optical fibre 12. The surgical navigation system 80 can track the tracker 10 based on the detected light 24. FIG. 1 shows in an abstract manner that the light 24 radiates from the light emitting portion 22 in an angle perpendicular to the longitudinal extension of the optical fibre 12. The angle of the light radiation is not limited to such a perpendicular angle and may assume any other angle. The angle may depend on the impingement angle at the boundary and the way the light emitting portion 22 is realized. The diameter of the optical fibre 12 may be in the range of approximately 50 μm to 500 μm (e.g., approximately 100 μm). Consequently, the light emitting portion 22 is confined to a similarly narrow width, which allows very accurate tracking of the tracker 10.

The portion 22 shown in FIG. 1 only covers a part of the circumference of the optical fibre 12. Therefore, the light 24 emitted by the portion 22 cannot be seen from a side of the optical fibre 12 facing away from the portion 22. Such a configuration is more light efficient and allows determining a rotational angle of the fibre 12. Alternatively, the portion 22 may extend around the entire circumference of the optical fibre 12.

FIG. 2A shows an optical fibre 12 with a circumferential light emitting portion 22. Such a configuration allows the optical fibre 12 to emit light in an angle that extend around the entire circumference of the optical fibre 12. Therefore, the optical sensor (not shown) is able to detect the optical fibre 12 independently from its rotational angle around its longitudinal extension.

The portion 22 of the lateral surface of the optical fibre 12 that is configured to emit light 24 can be realized by at least one of the modifications described below. Any of those modifications are applicable to the optical fibre 12 shown in FIG. 2A.

In one modification, the core 18 and/or the cladding 20 may comprise fluorescent elements. The fluorescent elements are excitable by the light guided in the optical fibre 12. The light 24 is reemitted shortly after in a unidirectional manner. The reemitted light may exit the lateral surface of the optical fibre 12.

In another modification, the core and/or the cladding 20 may comprise scattering elements. The scattering elements divert the light at an angle that allows the light to exit the lateral surface of the optical fibre 12. Possible scattering elements are micro bubbles, a rough boundary between the core 18 and the cladding 20 or material modifications that render the core 18 and/or cladding 20 material diffusive.

Such scattering elements may be introduced by laser machining and by changing or manipulating the core and/or cladding material during the manufacturing of the optical fibre 12.

In another modification, the refractive index of the cladding and/or core material is modified. The closer the refractive index of the cladding material and the core material are, the smaller the critical angle $\theta_c$ becomes (see also equation 1). Therefore, the higher refractive index of the cladding material is, the lower the probability of a total reflexion becomes. When no total reflexion occurs, at least a part of the light exits the lateral surface of the optical fibre 12. The refractive index of the cladding material can be lower or higher than the refractive index of the core material. When the refractive index of the cladding material is lower than the refractive index of the core material, total reflection is still possible under angles steeper than the critical angle $\theta_c$ and emission from the lateral surface is still low. When the refractive index of the cladding material is higher than the refractive index of the core material, only partial reflexion occurs resulting in a higher emission from the lateral surface of the optical fibre 12.

In yet another modification, the geometry of the cladding 20 is altered. Examples of such modifications are shown in FIGS. 2B and 2C.

Figure 2B:
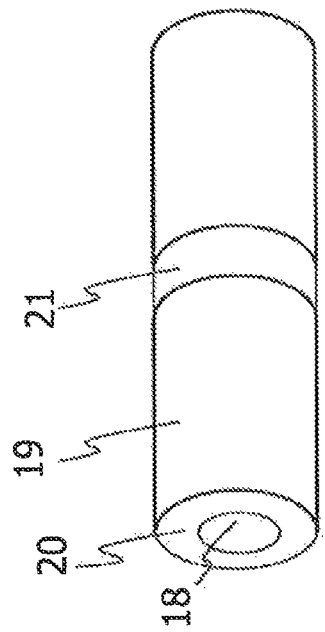
FIG. 2B shows an optical fibre with a tapered cladding.

FIG. 2B shows an optical fibre 12 wherein the cladding 20 has a tapering 26. In order to fulfil its function in a regular optical fibre 12, the cladding usually has a wall thickness of a few micrometres (e.g., 5 µm). By reducing the wall thickness of the cladding 20, the border between the core 18 and the cladding 20 may not exhibit total reflexion anymore. An optical fibre 12 with a sufficiently tapered (i.e., thinner) cladding 20 is configured to emit light 24 via the lateral surface. The cladding 20 may have a tapered wall thickness of less than 5 times, preferably 3 times, further preferably 1 time the wavelength of the light 24 guided by the optical fibre 12.

Figure 2C:
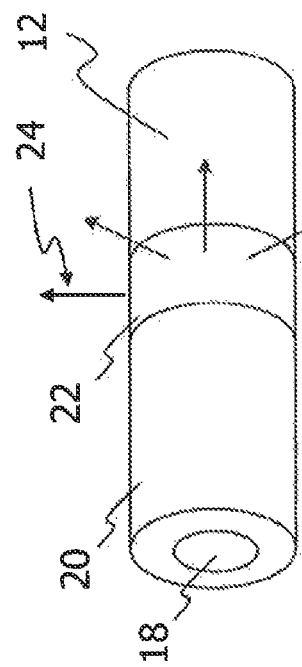
FIG. 2C shows an optical fibre, wherein the cladding has an opening.

FIG. 2C shows an optical fibre 12, wherein the cladding 20 has an opening 28. At the opening 28, the core 18 is not covered by any cladding material. Thus, in that area, the optical fibre 12 has no border between the core 18 and a cladding 20, which means no total reflection can occur. With no total reflexion, the optical fibre 12 is configured to laterally emit light at the opening 28.

Figure 2D:
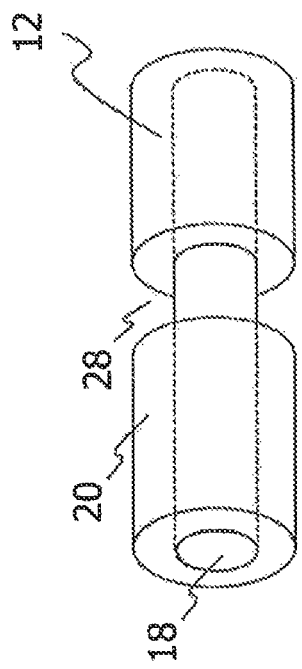
FIG. 2D shows an optical fibre further with a light absorbing sleeve.

FIG. 2D shows an optical fibre 12 with a light absorbing sleeve 19. The light absorbing sleeve 19 is configured to encase the optical fibre 12. Alternatively, the sleeve 19 may encase only a part of the optical fibre 12. The sleeve 19 has an opening 21. Alternatively, the sleeve 19 has an area of reduced light absorbance. Light emitted by the lateral surface of the optical fibre 12 is absorbed when impinging on the sleeve 19, but is not absorbed at the area where the sleeve 19 has the opening 21.

The opening 21 can be used to define the light emitting portion 22, or to additionally improve the definition of a light emitting portion 22 that is generated in another way as described above. In the first case, the optical fibre 12 may be configured to emit light via the entire lateral surface. To this end, any of the ways described above may be employed, such as fluorescent elements, scattering elements, roughened boundary, diffusive material, geometric modifications or a cladding 20 with a refractive index that is higher than the refractive index of the core 18. Wherever the sleeve 19 that covers the optical fibre 12 has an opening 21 (or a reduced light absorbance), light can exit the tracker 10. Therefore, the light emitting portion 22 is defined by the opening 21 of the sleeve 19.

In the latter case, the optical fibre 12 is already configured to emit light via at least a portion 22 of the lateral surface, as described above. However, such a portion 22 may not be defined well enough or some of a plurality of such portions 22 need to be obscured for a specific application. To this end, a light absorbing sleeve 19 as described above may be provided. At a light emitting portion 22 that does not need to be obscured the sleeve 19 has an opening or a reduced light absorbance. Due to the discrete border of the opening 21, the light emitting portion 22 can be better defined.

As described above, the light emitting portion 22 of the optical fibre 12 can extend over the entire circumference of the optical fibre 12 or only a part thereof. The portion 22 may also have any shape in a longitudinal direction. FIG. 3A-E show optical fibres 12 with different configurations for the light emitting portions 22.

FIG. 3A shows an optical fibre 12 wherein the light emitting portion 22 is an essentially point-shaped spot on the optical fibre 12. The longitudinal extension of the point-shaped light emitting portion 22 may be shorter than 2 times, preferably 1 time, or more preferably 0.5 times the diameter of the optical fibre 12. A surgical navigation system (not shown) can more accurately assign the portion 22 to a position in space if the dimensions of the portion 22 are small. Therefore, the point-shaped portion 22 may increase the accuracy of the tracking of the surgical navigation system.

It is noted that the portion 22 shown in FIG. 3A (as well as in FIGS. 3B to 3E) is illustrated as extending only over a part of the circumference of the optical fibre 12 (such as seen in FIG. 1). However, any of the portions 22 may as well extend over the entire circumference of the optical fibre 12 (such as seen in FIG. 2A).

FIG. 3B shows an optical fibre 12 with a plurality of light emitting portions 22. The light emitting portions 22 are arranged with equal distance between each other. Alternatively, the light emitting portions 22 may be arranged with varying distances between each other. The light emitting portions 22 may be grouped with another. The distance between the light emitting portions 22 may relate to a position of the light emitting portions 22 along the optical fibre 12 in a straight configuration as illustrated in FIGS. 3A to 3E. The distance between the light emitting portions 22 may increase or decrease along the optical fibre 12.

FIG. 3C shows an optical fibre 12 with a light emitting portion 22 that extends longitudinally along the optical fibre 12. The longitudinal portion 22 follows the shape of the optical fibre 12. Therefore, a surgical navigation system (not shown) that tracks the longitudinal portion 22 can determine the shape of the optical fibre 12 from the detected longitudinal portion 22.

FIG. 3D shows an optical fibre 12 with a plurality of light emitting portions 22 that extend longitudinally along the optical fibre 12. The plurality of light emitting portions 22 may be arranged equidistantly, non-equidistantly, grouped, or spaced dependent on position on the optical fibre 12 as described above in combination with FIG. 3B.

FIG. 3E shows an optical fibre 12 with a plurality of light emitting portions 22, wherein part of the light emitting portions 22 extends longitudinally, and the other part of the light emitting portions 22 is point-shaped. These two shapes of light emitting portions 22 may be combined in any other way. For example, in case the optical fibre 12 extends along a shape with corners and edges between the corners (e.g., a polygon), point-shaped portion 22 may be arranged at corners and longitudinal shaped portions 22 may be arrange along the edges.

Figure 4:
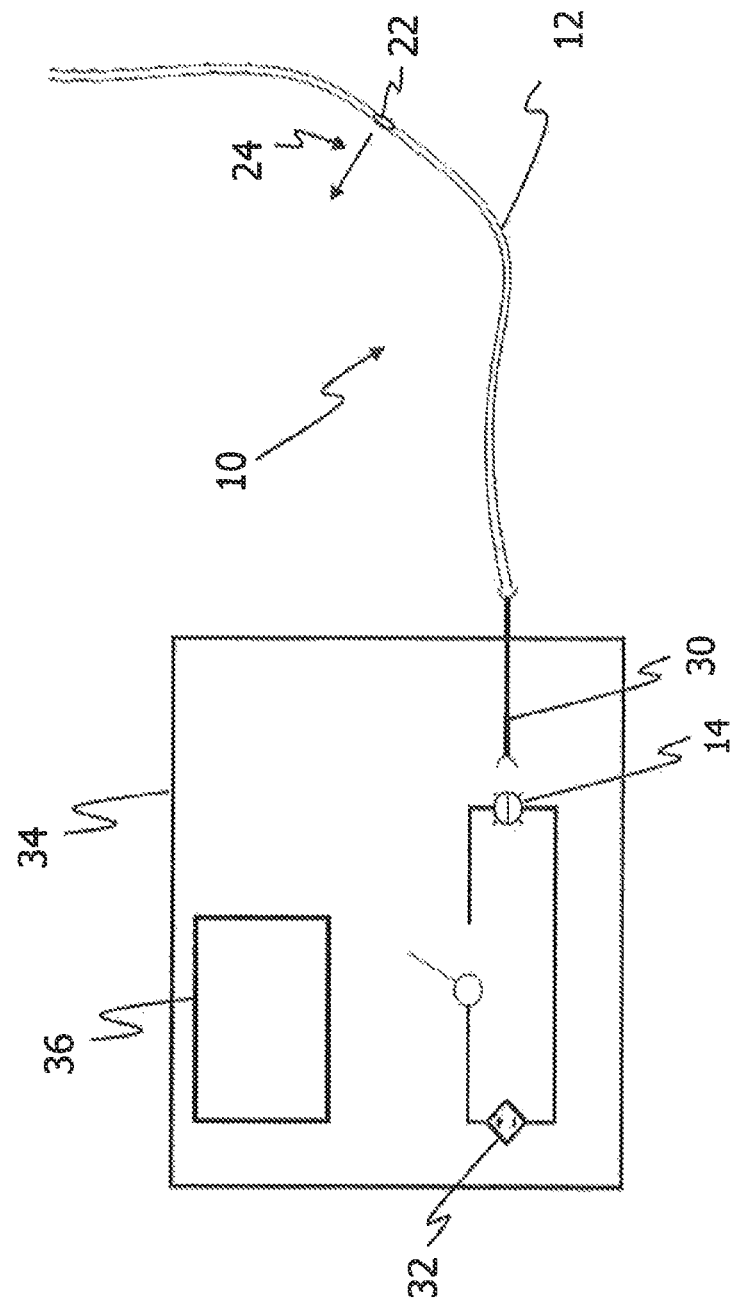
FIG. 4 shows a second embodiment of a tracker coupled with a light source.

FIG. 4 shows a second embodiment of a tracker 10 coupled with a light source 14. The tracker 10 comprises an optical fibre 12 that is configured to emit light 24 via at least one portion 22 of the lateral surface. The tracker 10 further comprises a connector 30 that is configured to optically couple the optical fibre 12 to the light source 14. The light source 14 is powered by a battery 32, wherein the light source 14 and the battery 32 are part of a light source device 34. Alternatively, the light source 14 may be powered by any other energy source such as an outlet, a device coupled with the light source device 34, or via wireless power transfer.

The light source device 34 further comprises or is coupled to a controller 36. The controller 36 is configured to control the light source 14. Controlling the light source 14 comprises switching the light source 14 on and off. It may further comprise control of a light intensity and/or operation frequency of the light source 14. The controller 36 may further be configured to power the light source 14. The controller 36 may be configured to communicate with the navigation system (not shown) and/or a light sensor of the navigation system. The controller 36 may be configured to communicate wirelessly or via a signal line.

With the tracker 10 being coupleable to the light source 14, the tracker 10 can be moved without having to move the weight of the light source 14. To this end, the optical fibre 12 may be provided with enough length to be movable around a surgical site. Alternatively, the tracker 10 may comprise the light source 14 or the light source device 34. In this case, the tracker 10 can be operated without being connected to another device. Therefore, the surgeon can move the tracker 10 more freely.

Figure 5:
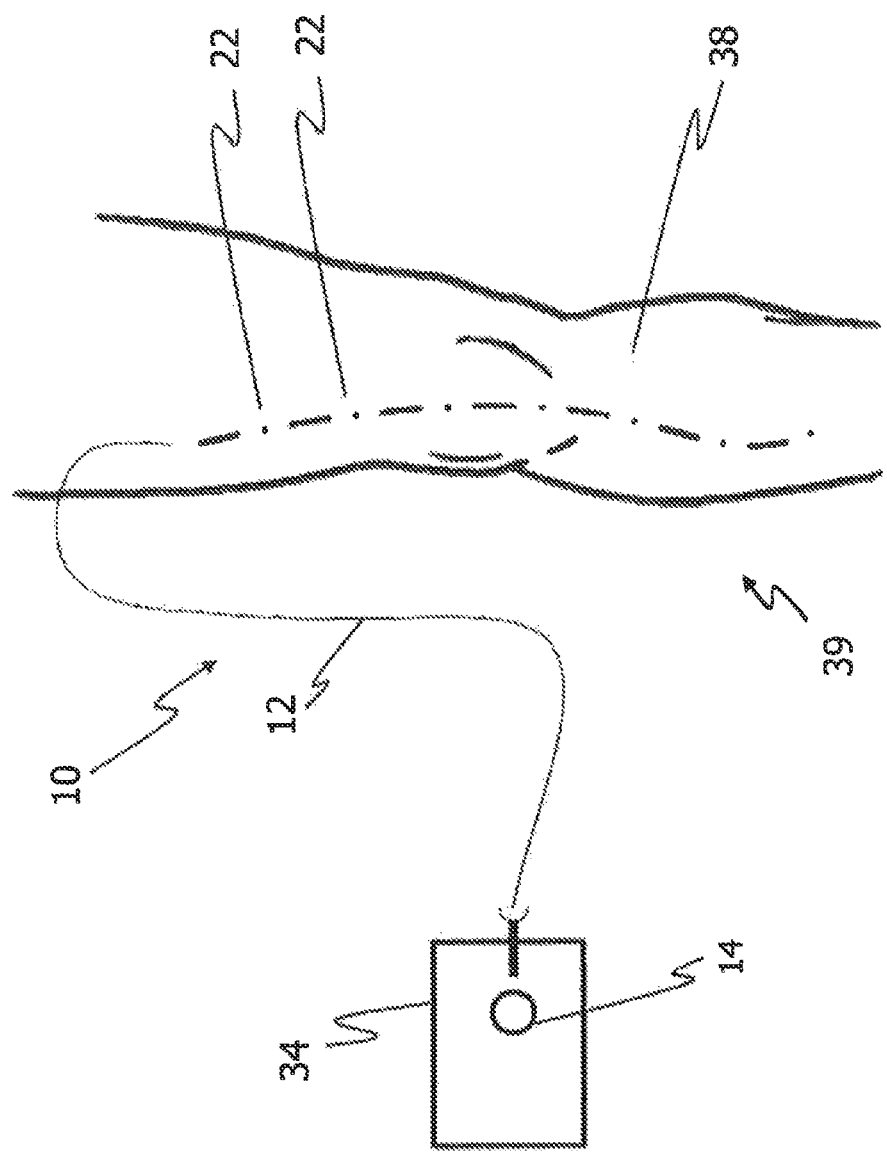
FIG. 5 shows a third embodiment of a tracker attached to the leg of a patient.

FIG. 5 shows the third embodiment of a tracker 10 attached to the leg 38 of a patient 39. The third tracker embodiment is essentially based on the second tracker embodiment but with a plurality of light emitting portions 22. Since the optical fibre 12 comprises a plurality of light emitting portions 22, a surgical navigation system (not shown) that tracks the tracker 10 is able to determine the pathway of the optical fibre 12 that extends along the leg 38. Therefore, movement of the leg 38 can be tracked by the surgical navigation system. In the third embodiment shown in FIG. 5, the optical fibre 12 is illustrated as a dashed and dotted line. The dots represent the light emitting portions and the dashes represent non-emitting portions in between. However, any of the patterns described above (particularly in combination with FIGS. 3A-E) can be used for the tracker 10.

The optical fibre 12 may further be configured to be stretchable in a direction along its longitudinal extension. If the tracker 10 is attached to two body parts that are connected by a joint, such as the knee joint in FIG. 5, the tracker 10 can adjust to the movement of the joint by stretching. The tracker 10 is less likely to detach from the body when strained. Furthermore, when being stretched, the light emitting portions 22 of the optical fibre 12 move apart. This movement may be detected by the surgical navigation system and be used to determine joint movement for a more accurate tracking of the body parts.

For the purpose of attaching the optical fibre 12 to the patient 39, the tracker 10 may comprise an adhesive (not shown). The adhesive may be applied directly to the optical fibre. Alternatively, the tracker 10 may further comprise a carrier (not shown in FIG. 5). The carrier may be a flexible elongated strip that supports the optical fibre. The elongated strip may comprise an adhesive configured to attach the carrier to the patient 39. Alternatively, the tracker 10 may not comprise an adhesive at all. In such a case, an adhesive may be applied to the patient 39 and the tracker 10 is then disposed onto the applied adhesive.

Figure 6:
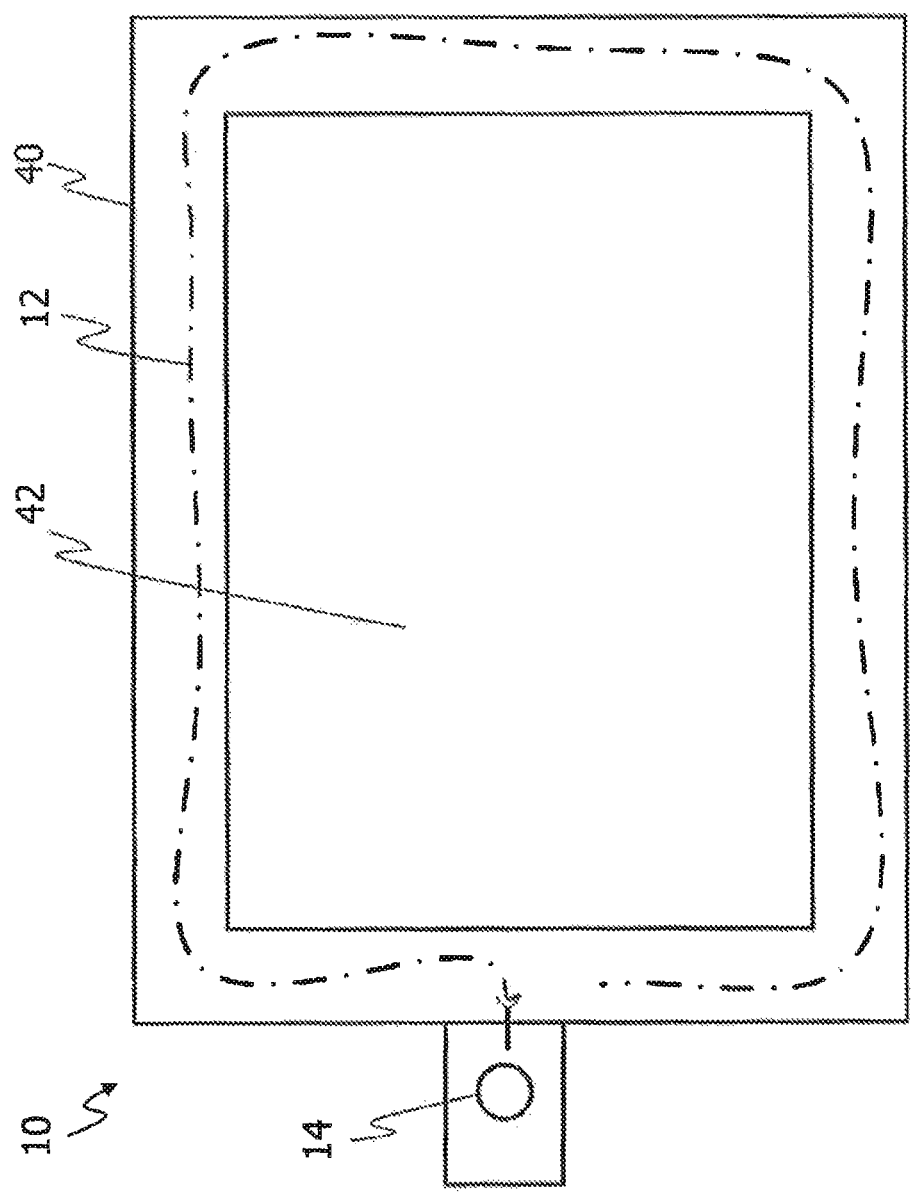
FIG. 6 shows a fourth embodiment of a tracker that has the shape of a frame enclosing a central opening.

FIG. 6 shows a fourth embodiment of the tracker 10 that has the shape of a frame enclosing a central opening 42. The tracker 10 comprises a carrier 40, wherein the carrier 40 supports the optical fibre 12. The tracker 10 comprises the light source 14. Alternatively, the tracker 10 may be coupleable to a separate light source. The carrier 40 is flexible and is configured to match the surface shape it is arranged on. Therefore, the carrier 40 can be arranged on any surface of a patient body (e.g., a patient's back). The carrier 40 may comprise a fabric or a polymer, like a foam or foil. The tracker 10 may comprise an adhesive configured to attach the carrier 40 to the surface of the patient body. Due to the close vicinity of the tracker 10 next to the surgical site, tracking of the patient and registration of patient data can be very accurate.

FIG. 7 shows a fifth embodiment of a tracker 10 comprising a carrier 40. The carrier 40 is rigid and supports the optical fibre 12. The optical fibre 12 extends on top of the surface of the carrier 40. Alternatively, at least a part of the optical fibre 12 may extend in or below the surface of the carrier 40. In case that at least a part of the optical fibre 12 is embedded inside the carrier 40, the carrier 40 may comprise translucent material. Therefore, the light emitted by the optical fibre 12 is visible from the outside. However, the carrier 40 may also comprise translucent material in the case that the optical fibre 12 is not embedded inside the carrier 40. The fibre 12 may thus still be visible to the light sensor or the surgeon from a side of the carrier 40 facing away the optical fibre 12.

The optical fibre 12 in FIG. 7 has four light emitting portions 22. Alternatively, the optical fibre 12 may have any other number of light emitting portions 22. A low number of light emitting portions 22, such as one or two, requires less light emission and is therefore more energy efficient. A larger number of light emitting portions 22, such as three, five or more allow tracking more degrees of freedom and/or provide better accuracy of the tracking due to redundancy.

The shape of the optical fibre 12 is fixed due to the rigidity of the carrier 40 that supports the optical fibre 12. Therefore, a spatial relationship between the light emitting portions 22 of the optical fibre is fixed and known a priori to a surgical navigation system. With the spatial relationship known to the surgical navigation system (e.g., stored on a memory that is comprised by or connected with the surgical navigation system), a position and/or orientation of the tracker 10 can be calculated based on the light emitting portions 22 detected by the light sensor of the surgical navigation system.

FIG. 7 further shows a light source 14 optically coupled to the optical fibre 12. The light source 14 is separate from the tracker 10 and therefore does not contribute to the weight of the tracker 10. Alternatively, the tracker 10 may comprise the light source 14. In such a case, the tracker 10 is easier to handle, since the tracker 10 is not connected to a separate device.

The tracker 10 comprises an interface 44 configured to couple the tracker 10 to a patient (not shown) or a surgical tool (not shown). The interface 44 shown in FIG. 7 comprises a base 46. The base 46 comprises an adhesive (not shown) that is configured to attach the tracker 10 with a surface, such as the patient of the surgical tool. Alternatively, the base 46 may comprise screw holes configured to receive screws.

Alternatively to the base 46, the interface 44 may comprise other elements for attaching the tracker 10 to the patient or surgical tool. For example, the interface 44 may comprise at least one of a clamp, a screw, a snap-in-connector, a screw thread and a magnet.

FIG. 8 shows a sixth embodiment of a tracker 10 similar to the one shown in FIG. 7. The carrier 40 has an edge 48, wherein the optical fibre 12 extends along the edge 48 of the carrier 40. The optical fibre 12 may extend along the entire edge 48 or only a part of the edge 48. The edge 48 extends in a plane. The plane also comprises a surface of the carrier 40. Since the optical fibre 12 is arranged on the edge 48, the visibility of the tracker 10 from the side and the top is improved. Therefore, the surgeon is provided with a larger range of orientation when operating the tracker 10.

FIG. 9A shows a first embodiment of a surgical tool system 50. The surgical tool system 50 comprises the tracker 10 as described above and a surgical tool 52 coupled to the tracker 10. The surgical tool 52 is only schematically depicted and may be a biopsy needle, a drill, a saw, a pointer, a cutter, a microscope or a measurement device. The surgical tool 52 may be a tool configured for use in surgeries related to ear, nose and throat (ENT). The surgical tool 52 may be a tool configured for use in neurosurgery (e.g., cranial surgery). The surgical tool 52 may be a tool that can be moved manually or a tool that is moved by a machine (such as a C-arm).

The surgical tool 52 shown in FIG. 9A has a longitudinal extension. The optical fibre 12 extends parallel to the longitudinal extension of the surgical tool 52. Alternatively, the optical fibre 12 may extend in a different configuration, such as in the helical shape or along a circumferential direction around the surgical tool 52.

The surgical tool 52 comprises a recess 54 or other means configured to receive the optical fibre 12 of the tracker 10. The recess 54 may be configured to receive the entire optical fibre 12 or a part thereof. The optical fibre 12 of the tracker 10 shown in FIG. 9A is fixed to the surgical tool 52 by a form fit connection between the optical fibre 12 and the recess 54. Alternatively, the optical fibre 12 may be fixed in the recess 54 by a strut or a translucent lid or by an adhesive.

FIG. 9B shows a cross-section of the surgical tool system 50. The optical fibre 12 is recessed into the surgical tool 52. A part of the optical fibre 12 extends out of the recess 54. Therefore, light emitted by one or more light emitting portions (not shown) is visible from the outside. Alternatively, at least a part of the optical fibre 12 may be completely embedded in the surgical tool 52. In such a case, at least a part of the surgical tool 52 may comprise a translucent material. Therefore, light emitted within the embedded portion of the optical fibre 12 may still be visible from the outside.

FIG. 9C shows a cross-section of a second embodiment of a surgical tool system 50 with multiple lines of optical fibre 12. The multiple lines of optical fibre 12 may be separate optical fibres 12 or the same optical fibre 12 extending back and forth along the surgical tool 52. The multiple lines of optical fibre 12 may have identical light emitting portions (not shown). In such a case the multiple lines provide redundancy for the visibility of the tracker 10 from all sides of the surgical tool 52. Alternatively, the multiple lines of optical fibre 12 may have geometrically different light emission characteristics. The different light emission characteristics may be at least one of different pattern of light emitting portion and different light spectra. The different characteristics of the multiple lines of optical fibre 12 allow determining an orientation of the surgical tool 52 around its circumference.

Figure 10:
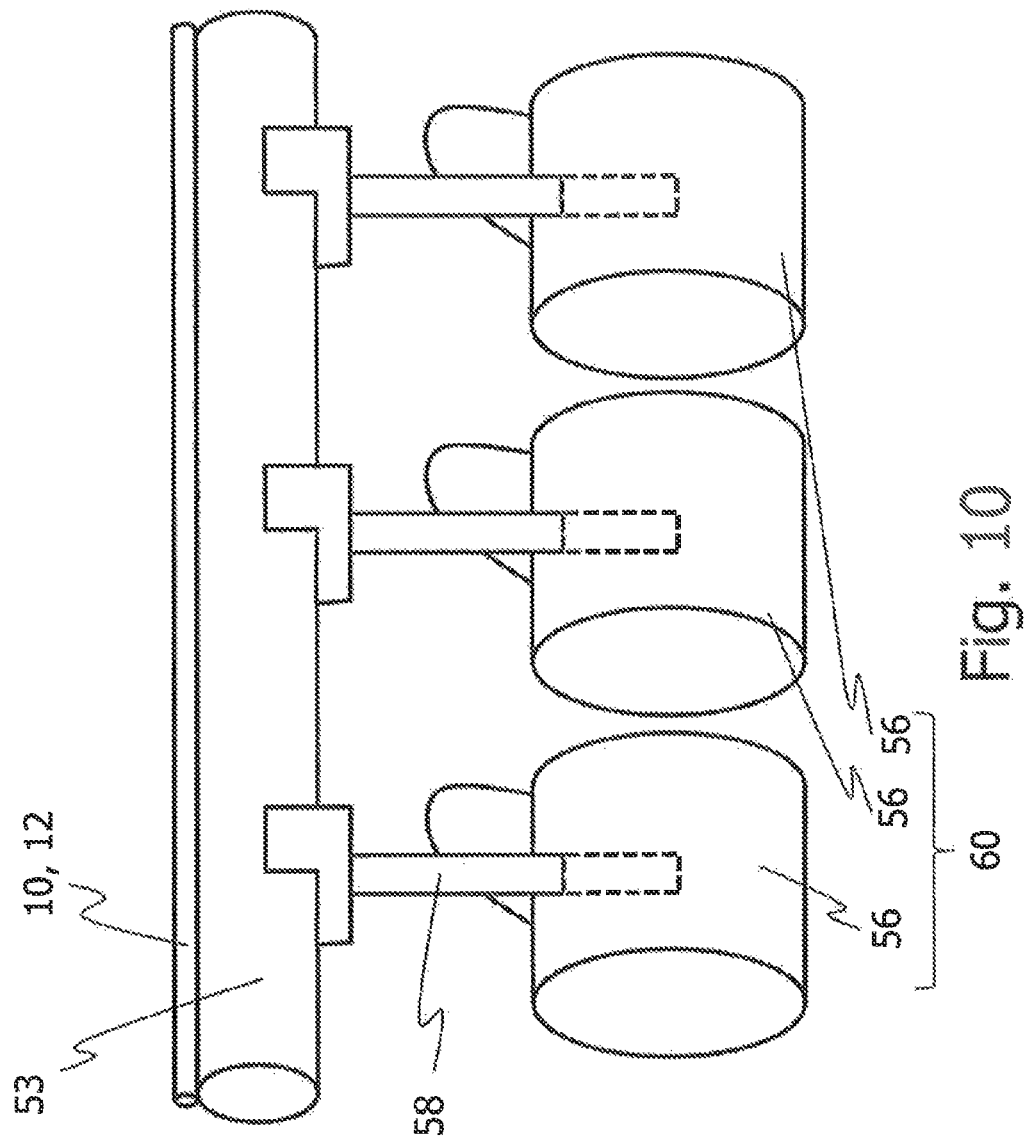
FIG. 10 shows a third embodiment of a surgical tool system comprising a surgical rod, wherein the rod is attached to vertebrae of a patient.

FIG. 10 shows a third embodiment of a surgical tool system 50 comprising a tracker 10 and a surgical rod 53, wherein the surgical rod 53 is attached to vertebrae 56 of a patient 39. The surgical rod 53 is attached to the vertebrae via screws 58, each of which is screwed into respective vertebrae 56. For the surgical tool system 50 shown in FIG. 10, the screws 58 are first screwed into the vertebrae 56, and thereupon the surgical rod 53 is attached to the screws 58. Alternatively, the screws 58 may already be attached to the surgical rod 53, wherein the screws 58 are screwed into the vertebrae 56 while being attached to the surgical rod 53.

The vertebrae 56 form a spine 60 with a longitudinal extension. Since the surgical rod 53 is attached to the spine 60 via the screws 58, the rod 53, as well as the optical fibre 12, follows the shape of the spine 60. By determining the shape of the optical fibre 12, the shape of the spine 60 may be calculated. Since a surgical navigation system with an optical sensor (not shown) can detect one or more light emitting portions of the optical fibre 12, the shape of the optical fibre 12, and therefore of the spine 60, can be determined by the surgical navigation system.

Figure 11B:
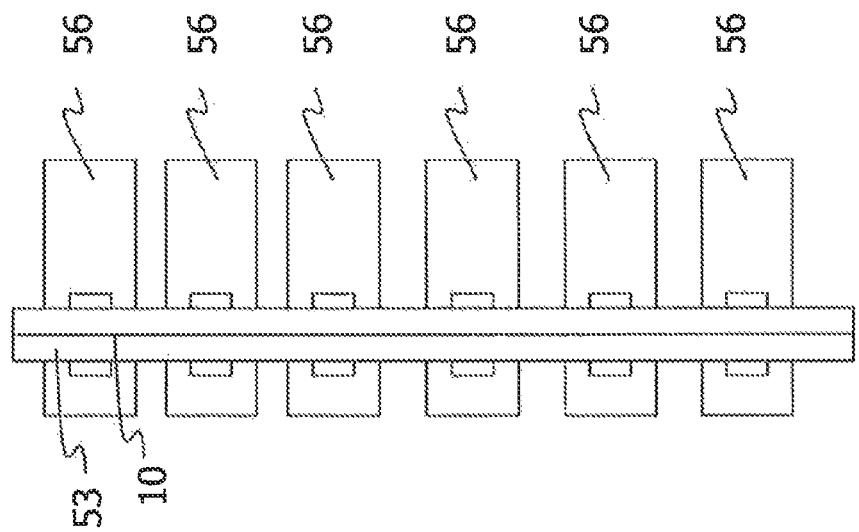
FIG. 11B shows the third embodiment of the surgical tool system of FIG. 11A after the shape of the spine was corrected.
Figure 11A:
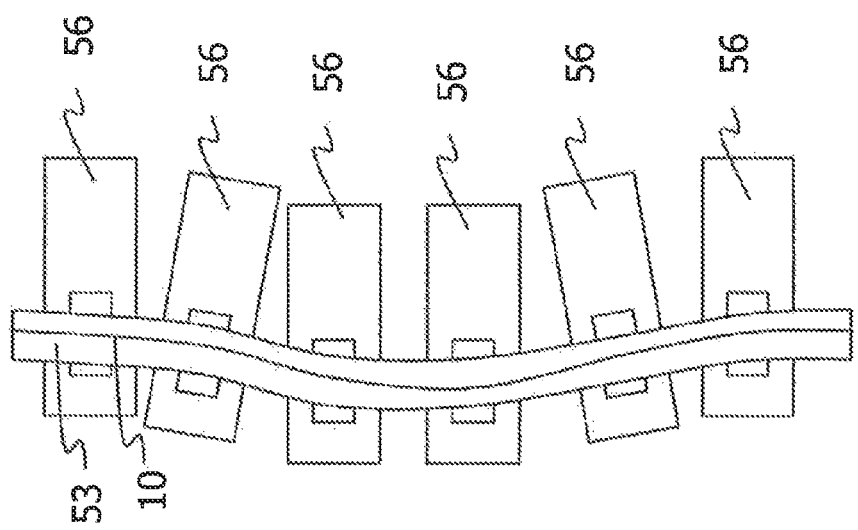
FIG. 11A shows the third embodiment of the surgical tool system attached to a spine with a sideway curve.

FIG. 11A shows the third embodiment of the surgical tool system 50 attached to a spine 60 with a sideway curve (scoliosis). The spine may have any other malformation such as an inward curvature (lordosis), an abnormally rounded upper back (kyphosis) or any combination thereof. During surgery, the surgeon corrects the curvature of the spine 60 by shaping the spine 60 into a more natural curvature. Particularly in the case of scoliosis, when viewed from the back of the patient 39, the spine 60 is to be straightened. Due to the complex shape of a healthy spine shape (double-s-form) correcting the shape is prone to errors. This error can be reduced by determining the shape of the spine via surgical navigation.

To this end, the optical sensor of the surgical navigation system (not shown) detects the light emitted by the one or more light emitting portions 22 of the surgical fibre 12. Based on the recorded image, the surgical navigation system is configured to determine the shape of the optical fibre 12, and therefore of the surgical rod 53 as well as of the spine 60. The surgeon may reshape the spine 60 until the shape of the optical fibre 12 (and the similarly shaped spine 60) reaches a target shape. The target shape may be calculated by the surgical navigation system. To this end, three-dimensional data of the patient (e.g., a CT scan) is registered with the tracker 10. The surgical navigation system continuously compares a target shape of the spine 60 with the current shape of the spine 60. The current and target shape of the spine 60 may be output by the surgical navigation system, for example on a display. The output may further comprise instructions to the surgeon for achieving the target shape.

The optical fibre 12 shown in FIG. 11A is configured to emit light via a portion that extends over the entire length of the optical fibre 12. Therefore, the surgeon also has vision of the entire optical fibre 12. Alternatively, the optical fibre 12 may have a plurality of light emitting portions. For example, the optical fibre 12 may have a light emitting portion located at each vertebra 56 (i.e., the corresponding screw 58), the surgical rod 53 is attached to.

FIG. 11B shows the third embodiment of the surgical tool system of FIG. 11A after the shape of the spine 60 was corrected. With FIGS. 11A and 11B showing a backside view of the spine 60 and the deformation to be corrected being a sideway curve, the corrected shape of the spine 60 shown in FIG. 11B is straight. The surgical rod 53 and the optical fibre 12 attached thereto are also straight. It is noted that straight in this context means that when viewed from the side, the spine 60 (as well as the surgical rod 53 and the optical fibre 12) would still have its natural double-s-shape.

FIG. 12A shows a fourth embodiment of a surgical tool system 50 with a tracker 10 attached to a surgical needle 55. The optical fibre 12 of the tracker 10 is recessed into the cannula of the needle 55 in a similar manner as described above for the surgical rod 53. Alternatively, the optical fibre 12 may at least partly extend on top or below the surface of the needle 55. The optical fibre 12 extends in the same direction as the extension of the needle 55.

Similar to the surgical tool system 50 with the surgical rod 53 as described above, the optical fibre 12 essentially describes the same shape as the surgical needle 55. Therefore, by determining the shape of the optical fibre 12, the shape of the surgical needle 55 can be determined.

The needle 55 may be bent prior to insertion of the surgical needle 55 into the patient (not shown) and/or upon insertion into the patient. Due to the bending of the surgical needle 55, the position of the tip of the surgical needle 55 is difficult to determine by the surgeon. The optical fibre 12 of the surgical tool system 50 is configured to emit light via at least a portion of its lateral surface. The emitted light can be detected by the optical sensor of the surgical navigation system, which enables the surgical navigation system to track the shape of the surgical needle 55 and its tip.

FIG. 12B shows the fourth embodiment of the surgical tool system of FIG. 12A, wherein the surgical needle 55 is bent. Consequently, the optical fibre 12 has essentially the same shape as the bent surgical needle 55.

In case the surgical needle 55 is inserted close to the surface of the patient, such as an arm vein, the optical fibre 12 may still be visible while inside the patient. In such cases, the surgical needle 55 may be tracked by the surgical navigation system further taking into account the light emitted from the portion of the surgical needle 55 that is inserted into the patient body. By this, the accuracy of the tracking can be further improved.

FIG. 13 shows a surgical navigation system 80 comprising a tracker 10 and an optical sensor 82. The surgical navigation system 80 can be used in connection with any of the tracker embodiments described herein.

The optical sensor 82 comprises a camera. The optical sensor 82 is configured to detect a light spectrum that is emitted by the optical fibre 12. The optical fibre 12 may emit in the visible spectrum, wherein the optical sensor 82 is configured to detect light in the visible spectrum. In addition or alternatively, the optical fibre 12 and the optical sensor 82 may operate in a different light spectrum, such as infrared or ultraviolet light. In such a case, the surgical navigation system 80 is less affected by ambient light.

The surgical navigation system 80 comprises a tracker 10 that is to be associated with a patient or a surgical tool. Alternatively, the surgical navigation system 80 may comprise a surgical tool system 50 as described above. The exemplary surgical tool system 50 as shown in FIG. 13 comprises a forceps 57. Alternatively, the surgical tool system 50 may comprise any other tool as described above. The tracker 10 comprises an interface 44 with a clamp 45. The clamp 45 engages the forceps 57 and attaches the tracker 10 thereto. Alternatively, the interface 44 may comprise any other element for attachment as described above.

The surgical navigation system 80 further comprises a navigation controller 84 that is configured to receive sensor data from the optical sensor 82. The navigation controller 84 may be part of the optical sensor 82 or a separate device. Alternatively, the navigation controller 84 may be a separate device that is not part of the surgical navigation system 80, such as a computer that manages patient data, but that can additionally be used to compute the sensor data of the optical sensor 82.

The surgical navigation system 80 may further comprise or be connected to an output device 86. The output device 86 comprises at least one of a display, a speaker, a beamer, and a haptic feedback device. The output device 86 is configured to output information and/or instructions that result from tracking the tracker 10. The output information may comprise at least one of a visual display of the tracked tracker 10, a visual display of the tracker 10 relative to registered patient data, and an acoustic signal indicative of a position of the tracker 10. The instructions may comprise at least one of a visual representation of a target shape, target position and target orientation of the tracker 10, and a voice output guiding the surgeon.

Figure 14:
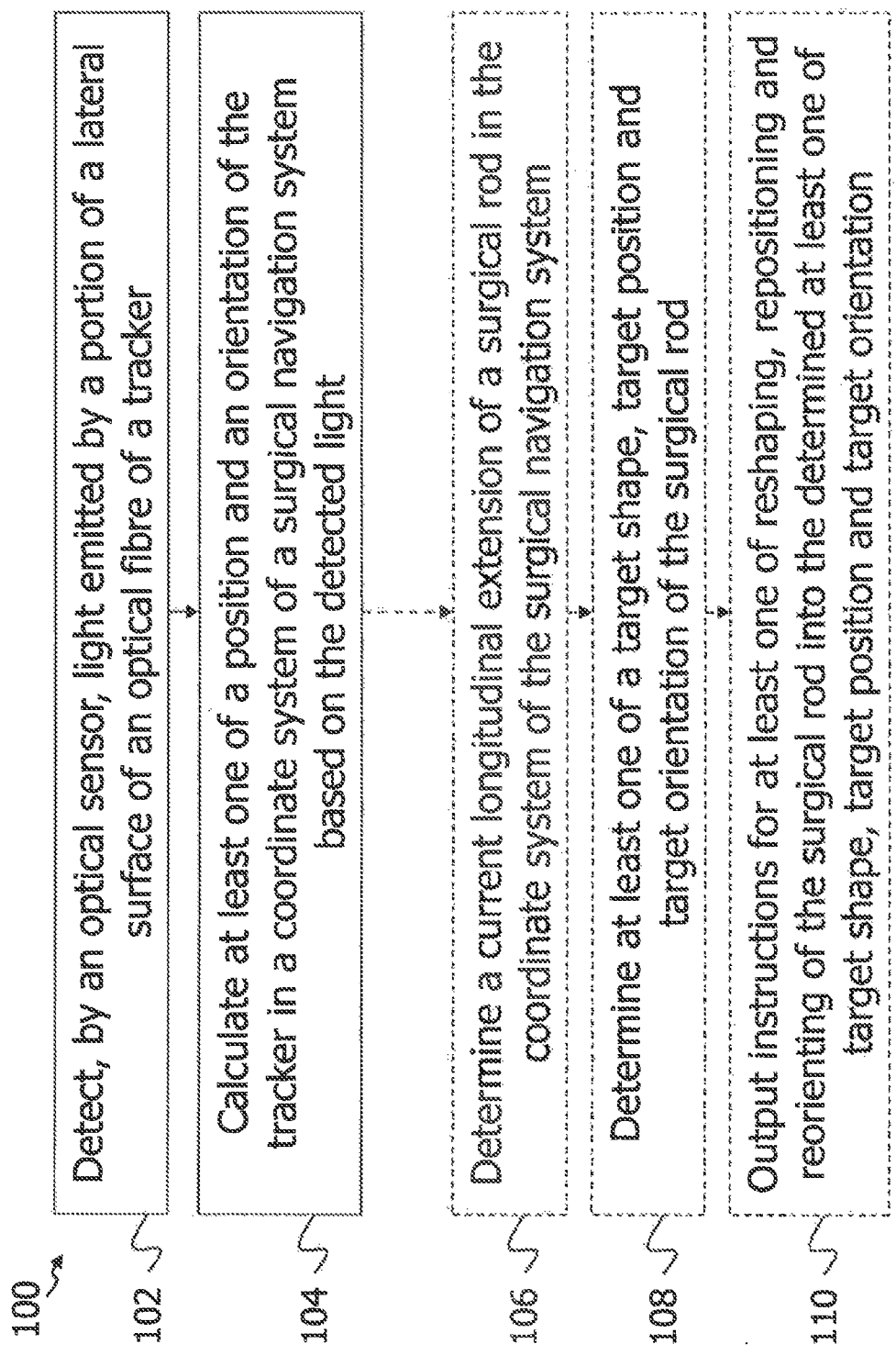
FIG. 14 shows a flow diagram of a method of operating a surgical navigation system.

FIG. 14 shows a flow diagram of a method 100 of operating a surgical navigation system. The steps 106, 108 and 110 are optional and therefore shown in text boxes with dashed lines.

The surgical navigation system comprises an optical sensor and a tracker with an optical fibre having a longitudinal extension and configured to be optically coupled to a light source such that the optical fibre transmits light emitted by the light source, wherein the optical fibre has lateral surface along its longitudinal extension and is configured to emit light via at least a portion of the lateral surface. Examples of such a tracker are described above.

The method comprises detecting in step 102, by the optical sensor 82, light emitted by the portion 22 of the lateral surface of the optical fibre 12. The light 24 may be continuously emitted by the light emitting portion 22 at an operation frequency, wherein the operation frequency is defined as the frequency in which light emitting portion 22 alternates between emitting and not-emitting. In such a case, the detecting may comprise synchronizing the optical sensor 82 with the operation frequency of the optical fibre 12. The synchronization reduces the power consumption of the tracker 10 and filters out noise signals with a different frequency.

The method 100 comprises calculating, in step 104, at least one of a position and an orientation of the tracker 10 in a coordinate system of the surgical navigation system 80 based on the detected light. The calculating step 104 may comprise knowledge of at least one of a longitudinal extension of at least one light emitting portion 22, a spatial relationship between light emitting portions 22, and an angular offset between light emitting portions 22 in a direction along the fibre circumference.

Optionally, the tracker 10 may be part of a surgical tool system 80 comprising the tracker 10 and a surgical rod 53, wherein at least a part of the optical fibre 12 of the tracker 10 extends along at least a portion of the surgical rod 53 (e.g., as seen in FIGS. 9 to 11). In such a case, the method 100 may comprise determining in step 106, a current longitudinal extension of the surgical rod 53 in the coordinate system of the surgical navigation system 80. The determining step 106 may comprise knowledge of at least one of a longitudinal extension of a light emitting portion 22, a spatial relationship between light emitting portions 22, and an angular offset between light emitting portions 22 in a direction along the fibre circumference.

The method 100 may further comprise determining in step 108, at least one of a target shape, target position and target orientation of the surgical rod 53. The determining step 108 may at least in part be based on three dimensional image data of the patient that is registered with the tracker and/or parameters set by the surgeon.

The method may further comprise outputting, in step 110, instructions for at least one of reshaping, repositioning and reorienting of the surgical rod into the determined at least one of target shape, target position and target orientation. The outputting step 110 may comprise outputting at least one of an image, a live feed, a video, a rendering, a sound, and a vibration. The instructions may be indicative of at least one of the respective target, distance from the respective target and actions to perform in order to reach the respective target.

The features described in relation to the exemplary embodiments shown in the drawings can be readily combined to result in different embodiments. It is apparent, therefore, that the present disclosure may be varied in many ways. Such variations are not to be regarded as a departure from the scope of the invention as defined by the claims appended hereto.

The invention claimed is:

1. A tracker configured to be associated with a surgical tool that is to be tracked by a surgical navigation system, the tracker comprising:
a rigid carrier including first and second surfaces and an edge that is at least partially defined by an intersection of the first and second surfaces at a non-zero angle;
an optical fiber having a longitudinal extension and configured to be optically coupled to a light source such that the optical fiber transmits light emitted by the light source, wherein the optical fiber is supported by the carrier with the longitudinal extension arranged on the edge; and
an interface configured to couple the tracker to the surgical tool, wherein the interface comprises at least one of a clamp, a screw, a snap-in-connector, and a magnet,
wherein the optical fiber has a lateral surface along its longitudinal extension and is configured to emit light via a plurality of spaced apart light emitting portions of the lateral surface that reside along the edge, the light emitting portions residing along the edge including a plurality of longitudinally-shaped light emitting portions and a plurality of point-shaped light emitting portions interspacing the longitudinally-shaped light emitting portions.

2. The tracker according to claim 1, wherein the light emitting portions are defined as first light emitting portions, and the optical fiber further comprises a core, a cladding surrounding the core and defining a plurality of spaced apart second light emitting portions, and a light absorbing sleeve configured to encase at least a part of the optical fiber, wherein the sleeve defines areas with openings or reduced light absorbances that define the first light emitting portions in cooperation with the second light emitting portions.

3. The tracker according to claim 1, wherein the optical fiber has two opposite ends and both ends of the optical fiber are configured to be optically coupled to the light source.

4. The tracker according to claim 1, wherein the carrier has the shape of a frame enclosing a central opening.

5. The tracker according to claim 1, wherein the first surface is entirely bounded by the edge, the longitudinal extension of the optical fiber is arranged along the entire edge so as to circumscribe the first surface, and the spaced apart light emitting portions reside along the edge so as to extend around the first surface.

6. The tracker according to claim 5, wherein the edge comprises a plurality of line segments and a plurality of corners defining a shape of the first surface, and the longitudinal extension is arranged along the entire edge such that a different one of the point-shaped light emitting portions is arranged at each of the corners and a different one of the longitudinally-shaped light emitting portions is arranged on each of the line segments.

7. The tracker according to claim 1, wherein the light source is separate from the rigid carrier supporting the optical fiber.

8. A surgical tool system comprising:
a surgical rod to be tracked by a surgical navigation system, the surgical rod attached to vertebrae of a spine using screws that are screwed into the respective vertebrae, and the surgical rod being bendable to follow a shape of the spine;
a tracker coupled to the surgical rod, the tracker comprising an optical fiber, the optical fiber having a longitudinal extension arranged along a longitudinal extension of the surgical rod, and the optical fiber configured to be optically coupled to a light source such that the optical fiber transmits light emitted by the light source, wherein the optical fiber has a lateral surface along its longitudinal extension and is configured to emit light via a plurality of spaced apart light emitting portions of the lateral surface that extend along the longitudinal extension of the rod, the light emitting portions extending along the longitudinal extension of the rod including a plurality of longitudinally-shaped light emitting portions and a plurality of point-shaped light emitting portions interspacing the longitudinally-shaped light emitting portions;
an optical sensor configured to detect light emitted by the optical fiber; and
a navigation controller coupled to the optical sensor and configured to:
determine a current shape of the surgical rod in a known coordinate system based on the detected light;
determine a target shape for the surgical rod based on a target shape for the spine; and
output instructions for reshaping the surgical rod based on the target shape and the current shape.

9. The surgical tool system according to claim 8, wherein the tracker is coupled to the surgical rod such that a different one of the point-shaped light emitting portions is arranged at each of the screws.

10. The surgical tool system according to claim 8, wherein the tracker is coupled to the surgical rod such that a different one of the spaced apart light emitting portions is arranged at each of the screws.

11. A surgical navigation system comprising:
a tracker configured to be associated with a surgical tool, the tracker comprising:
a rigid carrier including first and second surfaces and an edge that is at least partially defined by an intersection of the first and second surfaces at a non-zero angle;
an optical fiber having a longitudinal extension and configured to be optically coupled to a light source such that the optical fiber transmits light emitted by the light source, wherein the optical fiber is supported by the carrier with the longitudinal extension arranged on the edge, and wherein the optical fiber has a lateral surface along its longitudinal extension and is configured to emit light via a plurality of spaced apart light emitting portions of the lateral surface that reside along the edge, the light emitting portions residing along the edge including a plurality of longitudinally-shaped light emitting portions and a plurality of point-shaped light emitting portions interspacing the longitudinally-shaped light emitting portions; and an interface configured to couple the tracker to the surgical tool, wherein the interface comprises at least one of a clamp, a screw, a snap-in-connector, and a magnet; and an optical sensor configured to detect light emitted by the optical fiber.

12. The surgical navigation system according to claim 11, further comprising a navigation controller configured to calculate a position and/or an orientation of the tracker in a coordinate system of the surgical navigation system based on the detected light.

13. The surgical navigation system according to claim 11, further comprising the surgical tool.

14. The surgical navigation system according to claim 11, wherein the first surface is entirely bounded by the edge, the longitudinal extension of the optical fiber is arranged along the entire edge so as to circumscribe the first surface, and the spaced apart light emitting portions reside along the edge so as to extend around the first surface.

15. The surgical navigation system according claim 14, wherein the edge extends in a single plane and comprises a plurality of line segments and a plurality of corners defining a shape of the first surface, and the longitudinal extension is arranged along the entire edge such that a different one of the point-shaped light emitting portions is arranged at each of the corners and a different one of the longitudinally-shaped light emitting portions is arranged on each of the line segments.

16. The surgical navigation system according to claim 11, wherein the light source is separate from the rigid carrier supporting the optical fiber.

17. A method of operating a surgical navigation system that comprises an optical sensor and a tracker including a rigid carrier and an optical fiber supported by the rigid carrier, the rigid carrier including a first surface bounded by an edge, and the optical fiber having a longitudinal extension arranged on the edge, the tracker configured to be associated with a surgical tool that is to be tracked by the surgical navigation system, the method comprising:

coupling the optical fiber to a light source separate from the rigid carrier supporting the optical fiber such that the optical fiber transmits light emitted by the light source;

coupling the rigid carrier supporting the optical fiber to the surgical tool with an interface, wherein the interface comprises at least one of a clamp, a screw, a snap-in-connector, and a magnet;

emitting light from a plurality of spaced apart light emitting portions of a lateral surface of the longitudinal extension of the optical fiber arranged on the edge of the rigid carrier, the light emitting portions arranged on the edge of the rigid carrier including a plurality of longitudinally-shaped light emitting portions and a plurality of point-shaped light emitting portions interspacing the longitudinally-shaped light emitting portions;

detecting, by the optical sensor, the light emitted from the spaced apart light emitting portions of the lateral surface of the optical fiber; and calculating at least one of a position and an orientation of the tracker in a coordinate system of the surgical navigation system based on the detected light.

18. A method of operating a surgical navigation system that includes an optical sensor and a tracker including an optical fiber, the tracker configured to be associated with a surgical rod to be tracked by the surgical navigation system and to be attached to vertebrae of a spine, the method comprising:

coupling the optical fiber to a light source such that the optical fiber transmits light emitted by the light source via a plurality of spaced apart light emitting portions extending along a lateral surface of a longitudinal extension of the optical fiber, the light emitting portions including a plurality of longitudinally-shaped light emitting portions and a plurality of point-shaped light emitting portions interspacing the longitudinally-shaped light emitting portions;

coupling the optical fiber to the surgical rod such that at least a part of the lateral surface of the optical fiber extends along a longitudinal extension of the surgical rod;

attaching the surgical rod to vertebrae of a spine using screws that are screwable into the respective vertebrae, the surgical rod being bendable to follow the shape of the spine;

emitting light from the spaced apart light emitting portions of the optical fiber;

detecting, by the optical sensor, the light emitted from the spaced apart light emitting portions of the optical fiber;

determining a current shape of the surgical rod in a coordinate system of the surgical navigation system based on the detected light;

determining a target shape for the surgical rod based on a target shape for the spine; and outputting instructions for reshaping the surgical rod based on the target shape and the current shape.

19. The method according to claim 18, further comprising:

determining a current position and orientation of the surgical rod;

determining a target position and target orientation for the surgical rod based on a target portion and target orientation for the spine; and outputting instructions for repositioning and reorienting of the surgical rod into the determined target position and target orientation from the current position and current orientation, respectively.

* * * * *